United States Patent
Konawa

(10) Patent No.: US 11,207,221 B2
(45) Date of Patent: Dec. 28, 2021

(54) ABSORBENT ARTICLE

(71) Applicant: DAIO PAPER CORPORATION, Ehime (JP)

(72) Inventor: Satoko Konawa, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 195 days.

(21) Appl. No.: 15/554,510

(22) PCT Filed: Mar. 25, 2016

(86) PCT No.: PCT/JP2016/059580
§ 371 (c)(1),
(2) Date: Aug. 30, 2017

(87) PCT Pub. No.: WO2016/158731
PCT Pub. Date: Oct. 6, 2016

(65) Prior Publication Data
US 2018/0042782 A1    Feb. 15, 2018

(30) Foreign Application Priority Data

Mar. 27, 2015   (JP) .............................. JP2015-066944

(51) Int. Cl.
| | |
|---|---|
| *A61F 13/15* | (2006.01) |
| *A61F 13/47* | (2006.01) |
| *A61F 13/535* | (2006.01) |
| *A61F 13/534* | (2006.01) |
| *A61F 13/53* | (2006.01) |
| *A61F 13/51* | (2006.01) |

(52) U.S. Cl.
CPC .............. *A61F 13/47* (2013.01); *A61F 13/15* (2013.01); *A61F 13/534* (2013.01); *A61F 13/535* (2013.01); *A61F 2013/53445* (2013.01)

(58) Field of Classification Search
CPC .......... A61F 13/15; A61F 13/47; A61F 13/53; A61F 13/51; A61F 13/534; A61F 13/535; A61F 2013/53445; C08L 77/00; A01K 23/00; A47L 13/17
See application file for complete search history.

(56) References Cited

U.S. PATENT DOCUMENTS

| | | | |
|---|---|---|---|
| 7,759,540 B2 * | 7/2010 | Litvay .................. | A61F 13/535 604/367 |
| 2013/0226120 A1 * | 8/2013 | Van De Maele ... | A61F 13/5323 604/372 |

* cited by examiner

*Primary Examiner* — Tatyana Zalukaeva
*Assistant Examiner* — Ilya Y Treyger
(74) *Attorney, Agent, or Firm* — Wenderoth, Lind & Ponack, L.L.P.

(57) ABSTRACT

An absorbent article, such as a sanitary napkin, a pantiliner or an incontinence pad, which improves diffusion property of a body fluid and maintains a stable absorption amount. In FIG. 3, a sanitary napkin (1) includes an absorber (4) including an upper layer sheet (10) disposed at a skin side, a lower layer sheet (11) disposed at a non-skin side, and a highly water-absorbing polymer (12) disposed between the upper layer sheet (10) and the lower layer sheet (11). The upper layer sheet (10) is provided with a plurality of protruding portions (14) bulging out to the skin side and forming space portions (13) to be filled with the highly water-absorbing polymer (12), and a joined portion (15) in which the upper layer sheet (10) and the lower layer sheet (11) are joined to each other intermittently on the peripheral edges of the protruding portions (14) along the circumferential directions.

5 Claims, 13 Drawing Sheets

[Fig. 1]
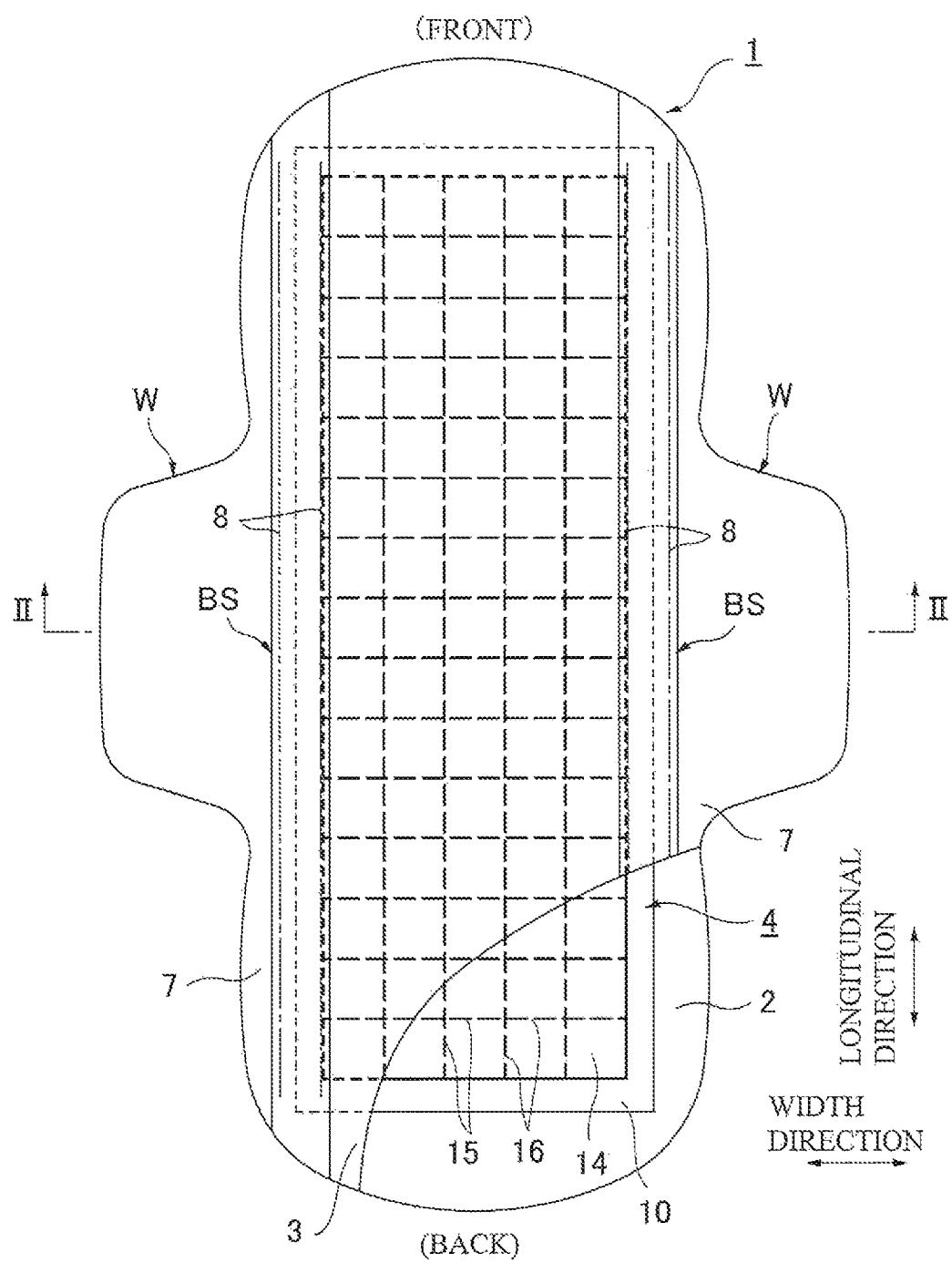

[Fig. 2]
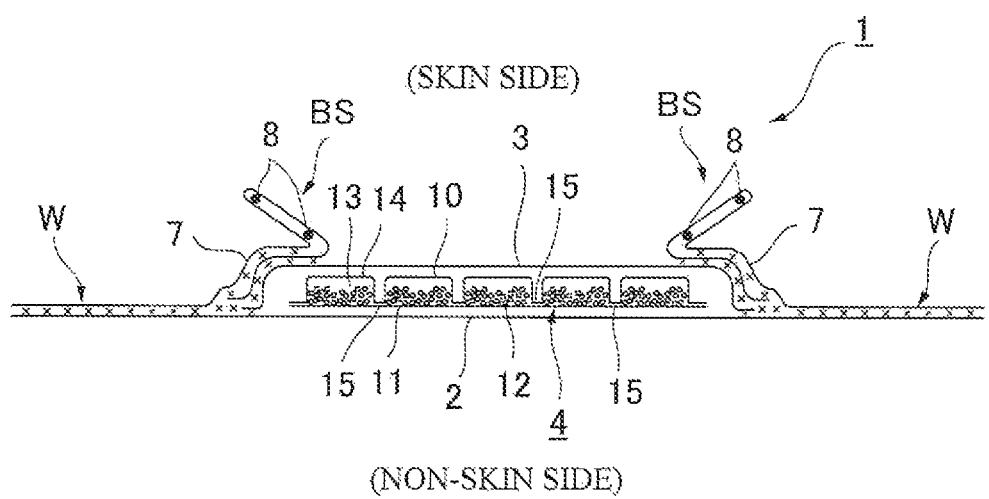

[Fig. 3]
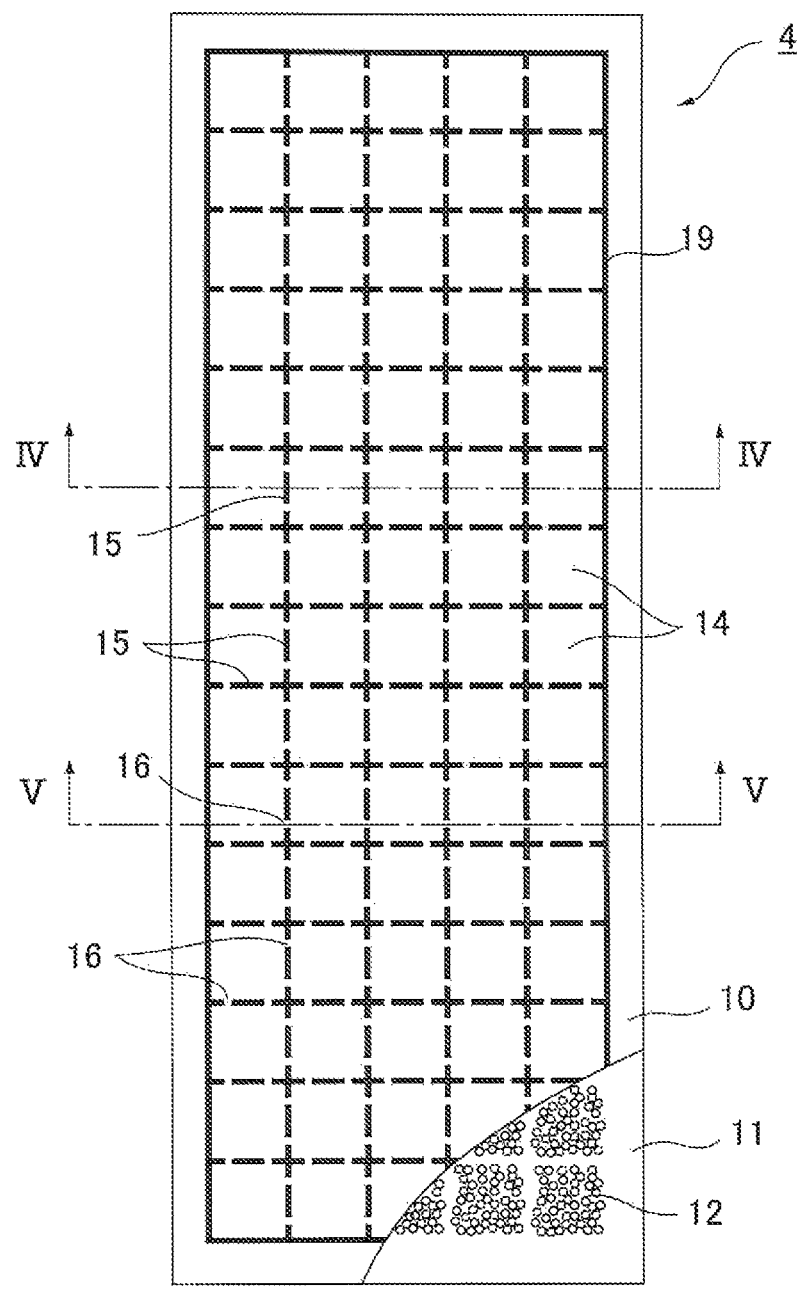

[Fig. 4]
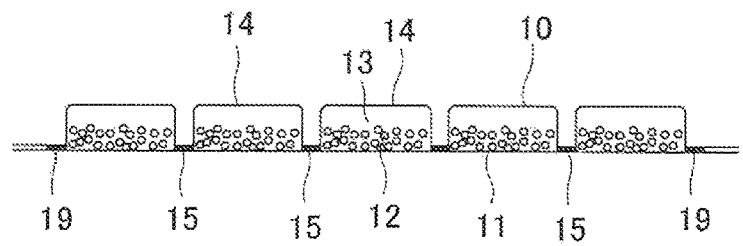
[Fig. 5]
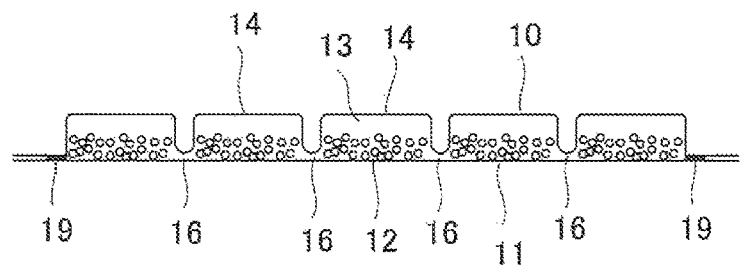
[Fig. 6]
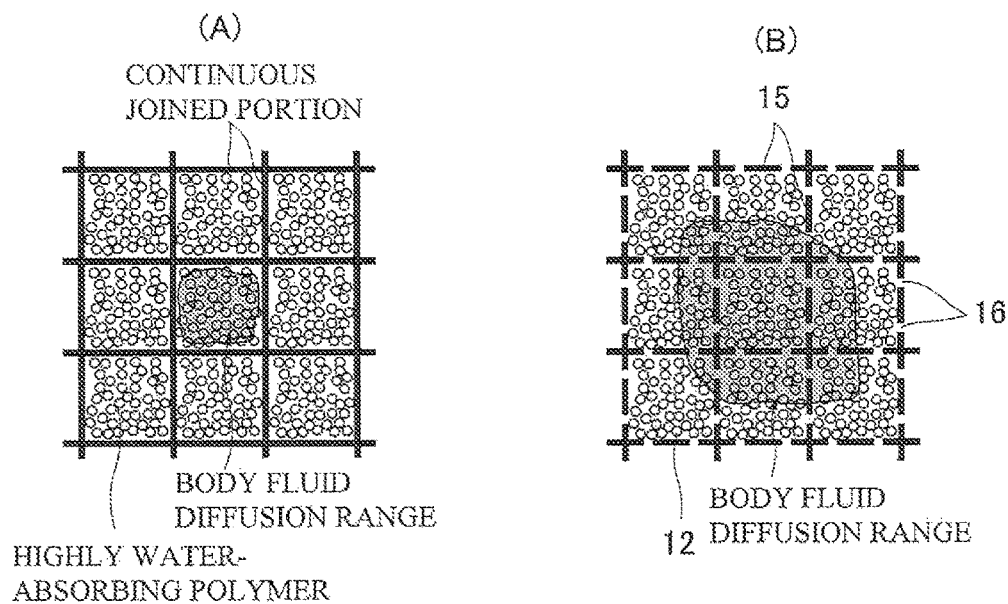

[Fig. 7]
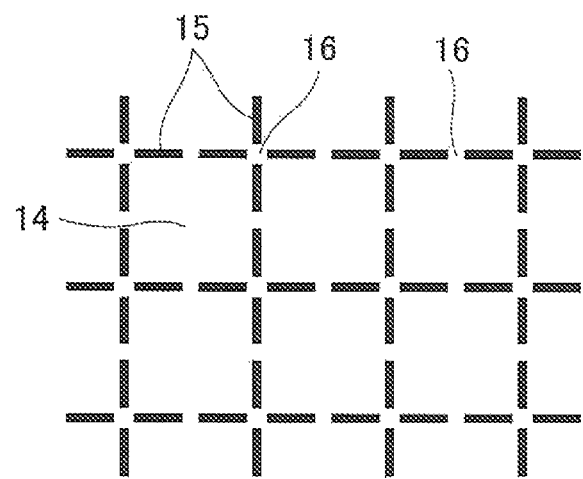

[Fig. 8]
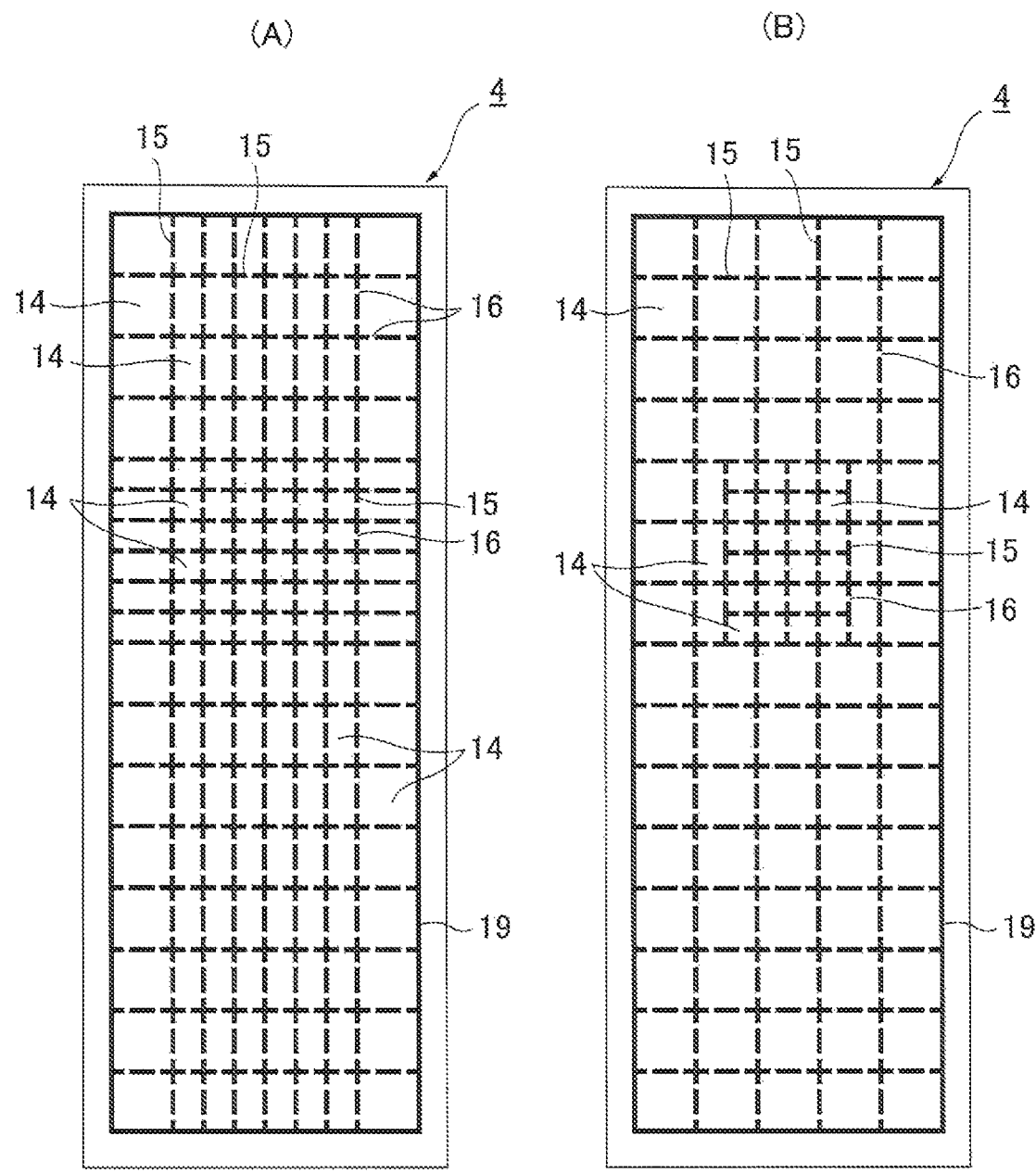

[Fig. 9]
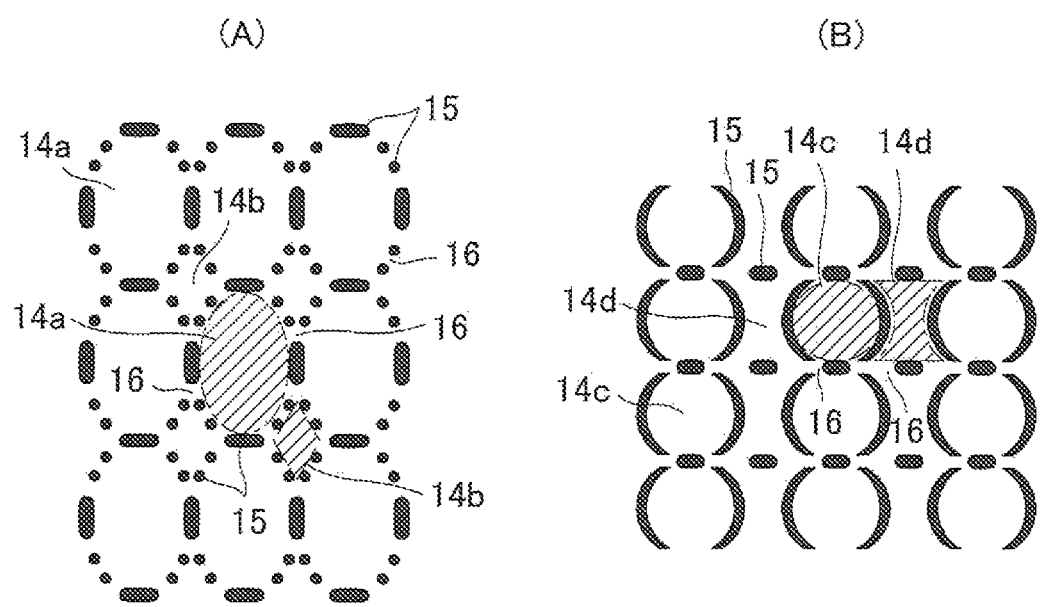

[Fig. 10]
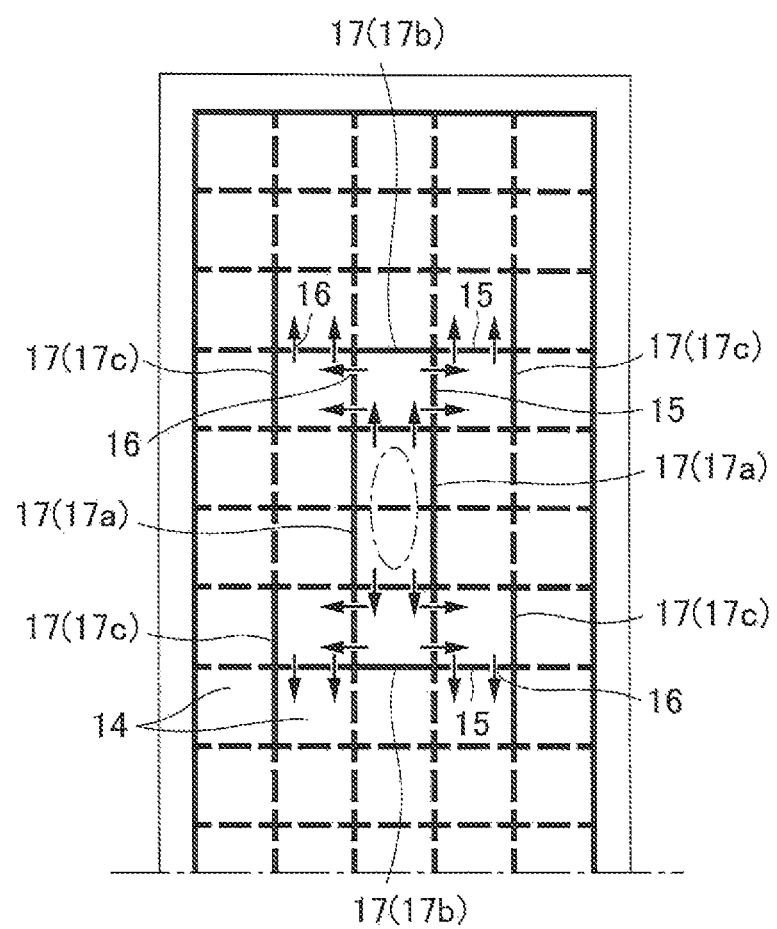

[Fig. 11]
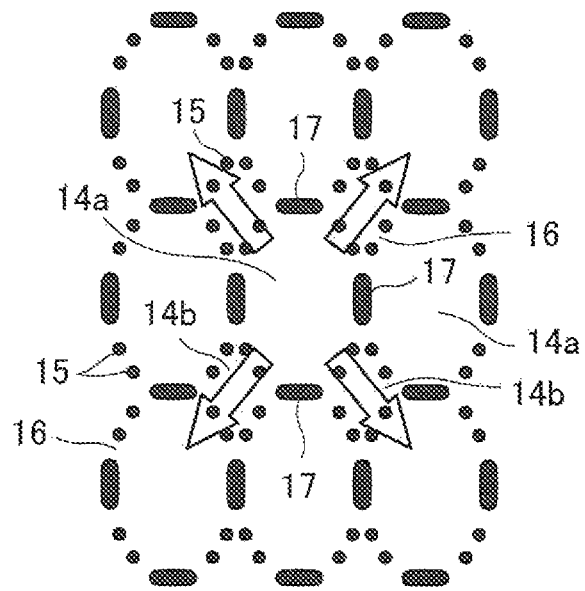
[Fig. 12]
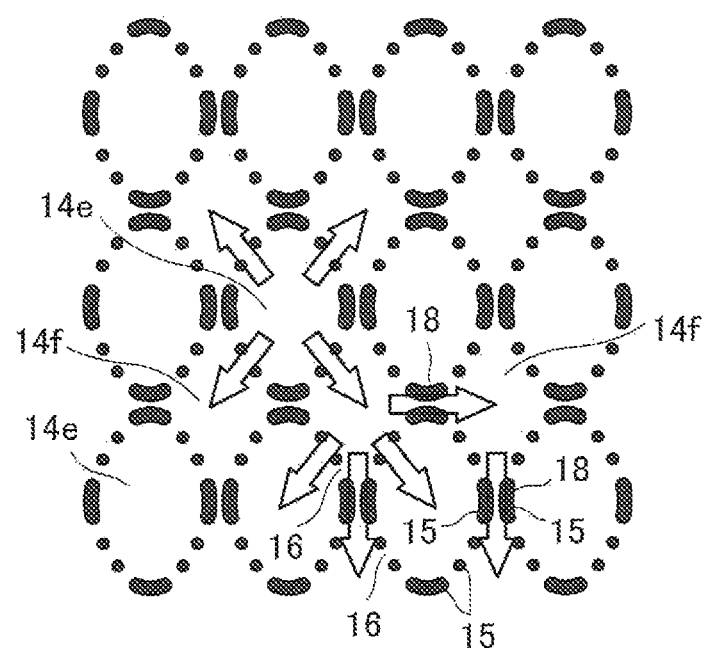

[Fig. 13]
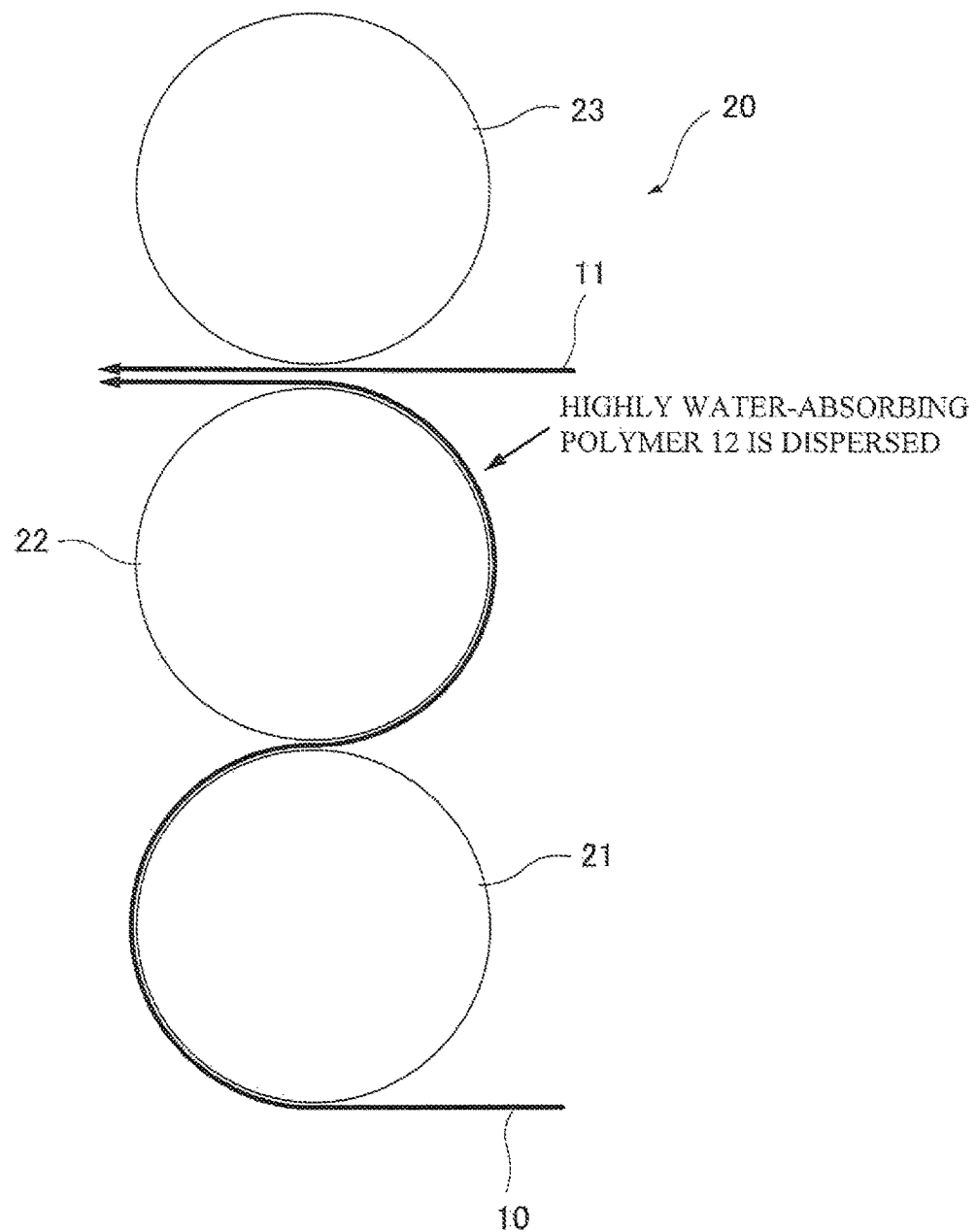

[Fig. 14]
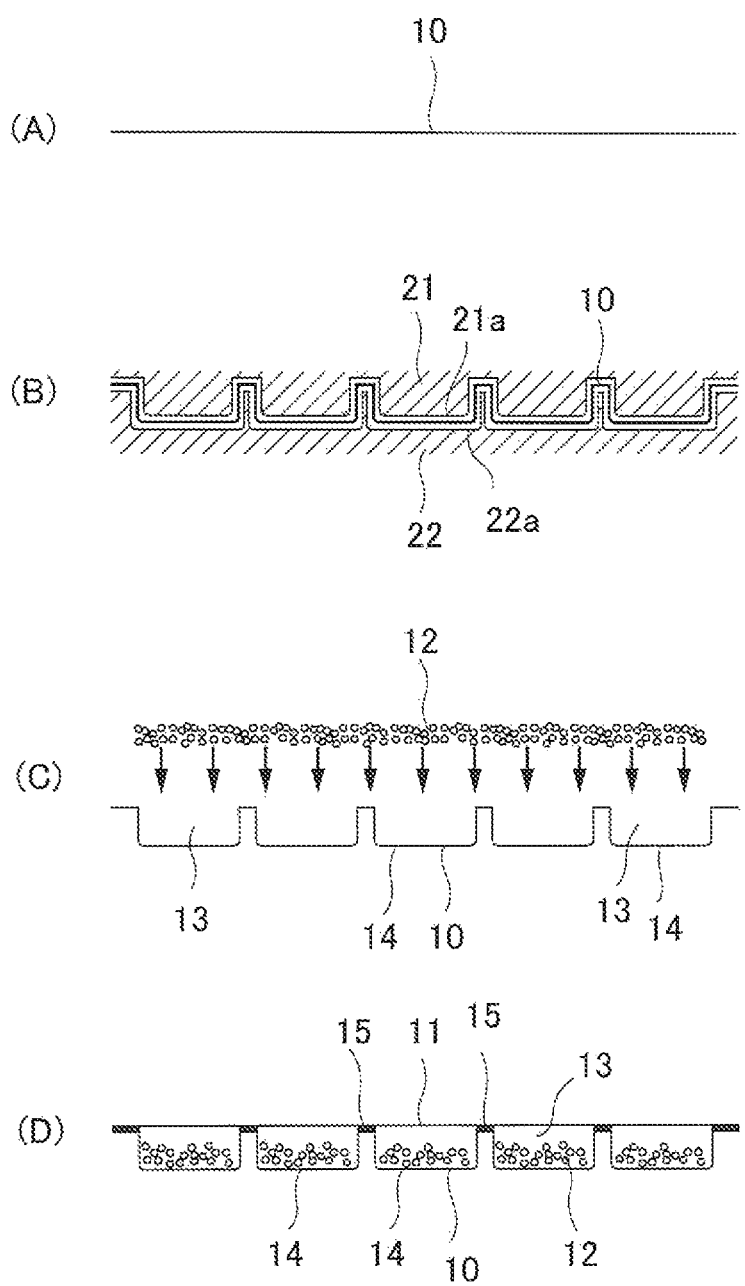

[Fig. 15]
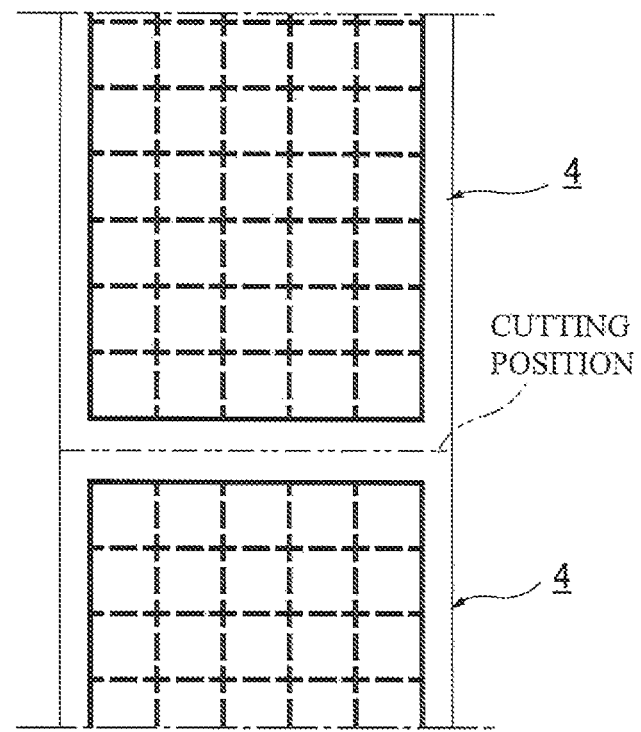

[Fig. 16]
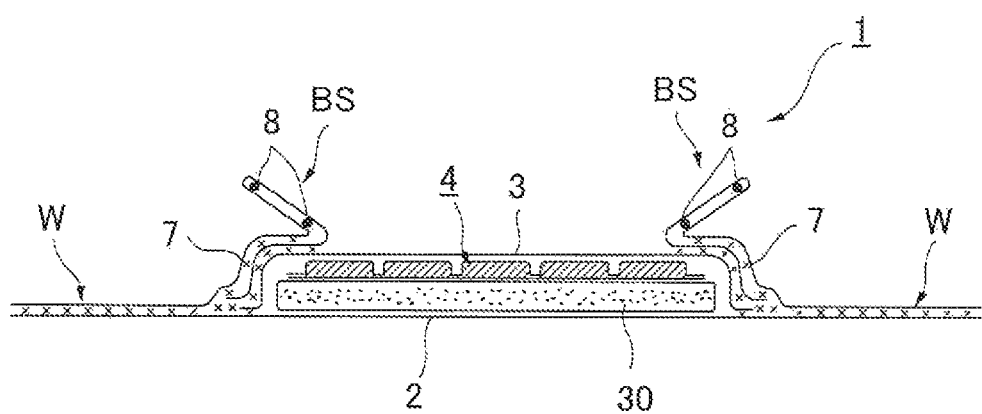
[Fig. 17]
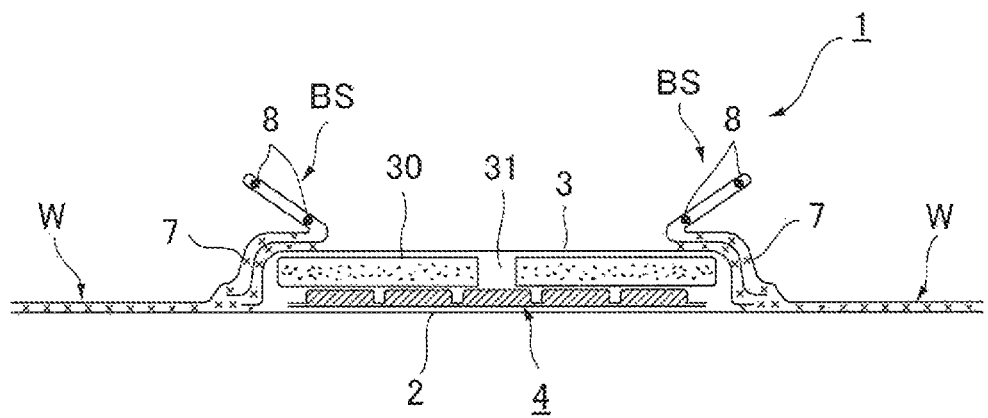

ABSORBENT ARTICLE

TECHNICAL FIELD

The present invention relates to an absorbent article such as a sanitary napkin, a pantiliner, and an incontinence pad, and more particularly to an absorbent article including an absorber that includes an upper layer sheet, a lower layer sheet, and a highly water-absorbing polymer therebetween.

BACKGROUND ART

Conventionally, as the absorbent articles, an absorbent article including a liquid-impermeable back-surface sheet such as a polyethylene sheet or a polyethylene sheet laminate non-woven fabric, a liquid-permeable front-surface sheet such as non-woven fabric or a permeable plastic sheet, and an absorber having a function of absorbing and retaining a body fluid and interposed between the liquid-impermeable back-surface sheet and the permeable front-surface sheet, has been known.

Various improvements have been made to absorbent articles of this type. As the absorber, an absorber having a structure in which a highly water-absorbing polymer is disposed between two sheets has been proposed. For example, the below-mentioned Patent Literature 1 discloses an absorption sheet including an upper surface sheet, a lower surface sheet and an absorption polymer interposed therebetween, and having a pocket made of a non-joined portion whose periphery is surrounded by the joined portion that joins the upper surface sheet and the lower surface sheet and formed into a shape having a long axis direction and a short axis direction in the plan view, wherein the absorption polymer is disposed movably in the long axis direction of the pocket.

Furthermore, the below-mentioned Patent Literature 2 discloses an water-absorbing article including two sheets with highly water-absorbing polymer particles interposed therebetween, wherein one facing surface of one of the two sheets is provided with a first joint region in which a hot-melt adhesive for fixing polymer particles is applied and a second joint region surrounding the first joint region in which a hot-melt adhesive for sealing is applied, and the first joint region is joined to one of facing surfaces with the hot-melt adhesive for fixing polymer particles.

Furthermore, the below-mentioned Patent Literature 3 discloses an absorbent article, in which an absorber includes a polymer particles-containing layer having absorbent polymer particles which are movable inside the absorber, wherein the polymer particles-containing layer includes a plurality of first restricting portions extending from one end to the other end in the width direction of the absorber and restricting the movement of absorbent polymer particles in the longitudinal direction, and second restricting portions which extends in a region partitioned by the adjacent first restricting portions at a length shorter than the length in the longitudinal direction of the partitioned region and along the longitudinal direction and which restricts the movement of the absorbent polymer particles in the width direction.

PRIOR ART LITERATURES

Patent Literatures

Patent Literature 1: Japanese Patent Application Unexamined Publication No. 2009-131510
Patent Literature 2: Japanese Patent Application Unexamined Publication No. 2012-152471
Patent Literature 3: Japanese Patent Application Unexamined Publication No. 2012-115390

SUMMARY OF INVENTION

Technical Problem

However, in the absorption sheet described in the Patent Literature 1 mentioned above, since an absorption polymer before absorbing water can freely move in a pocket provided over the width direction of the absorption sheet, the absorption polymer may be in one side in the pocket depending on the posture of a wearer, and the body fluid may not be efficiently absorbed by the absorption polymer.

Furthermore, in the absorption sheet described in the Patent Literature 2 mentioned above, since polymer particles are joined between two sheets with hot-melt adhesives, diffusion property of the body fluid penetrating between the two sheets is poor in the plane direction, and the body fluid is not likely to be efficiently absorbed by the polymer particles.

Furthermore, in the absorption sheet described in the Patent Literature 3 mentioned above, the movement of polymer particles is restricted by the first restricting portion and the second restricting portion. However, for example, when the absorber absorbs a large amount of body fluid, the polymer particles may move beyond the restricting portion on the flow of the body fluid. In such a case, a stable absorption amount by the absorber is not likely to be maintained.

Thus, a main object of the present invention is to provide an absorbent article capable of improving diffusion property of a body fluid and maintaining a stable absorption amount.

Solution to Problem

In order to solve the above problems, as the present invention according to claim 1, there is provided an absorbent article including an absorber that includes an upper layer sheet disposed at a skin side, a lower layer sheet disposed at a non-skin side, and a highly water-absorbing polymer disposed between the upper layer sheet and the lower layer sheet. The upper layer sheet is provided with a plurality of protruding portions bulging out to the skin side and forming space portions to be filled with the highly water-absorbing polymer, and is also provided with joined portions in which the upper layer sheet and the lower layer sheet are joined to each other intermittently on the peripheral edges of the protruding portions along a circumferential direction.

In the invention according to claim 1, in the absorber in which the highly water-absorbing polymer is disposed between the upper layer sheet and the lower layer sheet, the upper layer sheet is provided with a plurality of protruding portions bulging out to the skin side and forming space portions to be filled with the highly water-absorbing polymer, and joined portions in which the upper layer sheet and the lower layer sheet are joined to each other intermittently on the peripheral edges of the protruding portions along the circumferential direction. Consequently, the body fluid penetrating through the upper layer sheet can quickly move to adjacent space portions through an intermittent part (a non-joined portion) of the joined portion disposed intermittently. Thus, diffusion property of the body fluid is improved in a plane direction. Furthermore, since the surrounding of the space portions is partitioned by the joined portions intermittently disposed along the circumferential direction on the peripheral edges of the protruding portions, a state in which the highly water-absorbing polymer is contained can be kept, so that a stable absorption amount can be maintained.

As the invention according to claim 2, the absorbent article described in claim 1 is provided, wherein a planar shape of the protruding portion includes one or a combination of two or more selected from the group consisting of a polygon, a rhombus, a circle, an ellipse, and an hourglass shape.

The invention according to claim 2 shows examples of the planar shape of the protruding portion, and when the protruding portion has a shape that is one or a combination of two or more selected from the group consisting of a polygon, a rhombus, a circle, an ellipse, and an hourglass shape, diffusion property of a body fluid is improved, and the body fluid can be efficiently absorbed by the highly water-absorbing polymer.

As the invention according to claim 3, there is provided the absorbent article according to claim 1 or 2, which includes a liquid-diffusion restriction joined portion in which a length of the joined portion is relatively increased.

In the invention according to claim 3 mentioned above, the liquid-diffusion restriction joined portion is provided by making a length of the joined portion be relatively longer than that of the other portion, thereby restricting the diffusion of a body fluid into a predetermined direction. In particular, it is preferable that the liquid-diffusion restriction joined portion is provided along the longitudinal direction at the both ends in a width direction of a region corresponding to a body fluid discharge site of a wearer. Thus, it is preferable to prevent a body fluid from diffusing in the width direction and leaking sideway.

As the invention according to claim 4, there is provided the absorbent article according to any one of claims 1 to 3, which includes a liquid guiding joined portion in which the joined portions, being respectively disposed at peripheral edges of the protruding portions adjacent to each other, are arranged in parallel at predetermined spaced intervals between the joined portions.

In the invention according to claim 4 mentioned above, by providing a liquid guiding joined portion in which the joined portions, being disposed on the peripheral edges of the protruding portions adjacent to each other, are arranged in parallel at predetermined spaced intervals between the joined portions, a body fluid is guided in a constant direction and prevented from leaking sideway from end portions in the width direction.

As the invention according to claim 5, there is provided the absorbent article according to any one of claims 1 to 4, which includes a peripheral edge joined portion in which the upper layer sheet and the lower layer sheet are joined to each other continuously on the peripheral edge portion of the absorber along a circumferential direction.

In the invention according to claim 5, the peripheral edge portion of the absorber is continuously joined by the peripheral edge joined portion, thereby preventing the highly water-absorbing polymer from dropping off from the peripheral edge of the absorber.

As the invention according to claim 6, there is provided the absorbent article according to any one of claims 1 to 5, wherein a polymer filling rate that is a ratio of a volume of the space portion to a volume of the highly water-absorbing polymer to be filled in the space portion is 10% or more and 70% or less.

In the invention according to claim 6, the filling rate of polymer to be filled in the space portion of less than 10% deteriorates the absorption efficiency of a body fluid, and the filling rate of more than 70% makes it difficult for the body fluid to diffuse. Therefore, the filling rate of polymer of the space portion is defined to be 10% or more and 70% or less.

As the invention according to claim 7, there is provided the absorbent article according to any one of claims 1 to 6, wherein a fiber aggregate layer including a water-absorbing fiber aggregate is disposed at a non-skin side or a skin side of the absorber.

In the invention according to claim 7, combining the absorber with the fiber aggregate layer further enhances the absorbing property of a body fluid.

Advantageous Effects of Invention

As described above in detail, the present invention can provide an absorbent article capable of improving the diffusion property of the body fluid and enabling a stable absorption amount to be maintained.

BRIEF DESCRIPTION OF DRAWINGS

FIG. 1 is a partially broken development view of a sanitary napkin 1 according to the present invention.

FIG. 2 is a sectional view taken along the line II-II of FIG. 1.

FIG. 3 is a plan view of an absorber 4.

FIG. 4 is a sectional view taken along the line IV-IV of FIG. 3 (a cross-sectional view passing through a joined portion 15).

FIG. 5 is a sectional view taken along the line V-V of FIG. 3 (a cross-sectional view passing through a non-joined portion 16).

FIG. 6A is a plan view showing a state in which a body fluid diffuses when a peripheral edge of a protruding portion is continuously joined, and FIG. 6B is a plan view showing a state in which a peripheral edge of a protruding portion 14 is intermittently joined.

FIG. 7 is a plan view showing a modified example of arrangement pattern of joined portions 15.

FIGS. 8A and 8B are plan views showing modified examples of protruding portions 14 of absorbers 4, respectively.

FIGS. 9A and 9B plan views showing modified examples of arrangement patterns of the protruding portions 14, respectively.

FIG. 10 is a plan view of an absorber 4 provided with liquid-diffusion restriction joined portions 17.

FIG. 11 is an expanded plan view showing a diffusion state of a body fluid when the liquid-diffusion restriction joined portion 17 is provided FIG. 12 is an expanded plan view showing a diffusion state of a body fluid when the liquid guiding joined portion 18 is provided.

FIG. 13 is a side view showing a manufacturing device 20 for an absorber 4.

FIGS. 14A to 14D are sectional views showing manufacturing procedures of the absorber 4.

FIG. 15 is a plan view showing a cutting position of continuous absorbers 4, 4.

FIG. 16 is a sectional view (1) of a sanitary napkin 1 according to another embodiment.

FIG. 17 is a sectional view (2) of a sanitary napkin 1 according to still another embodiment.

DESCRIPTION OF EMBODIMENT

Hereinafter, exemplary embodiments of the present invention will be described in detail with reference to drawings.

Basic Configuration of Sanitary Napkin 1

As shown in FIGS. 1 and 2, a sanitary napkin 1 of the present invention includes an absorber 4 having a structure including a liquid-impermeable back-surface sheet 2 made of a polyethylene sheet, a polypropylene sheet, and the like, a liquid-permeable front-surface sheet 3 that allows menstrual blood and vaginal discharge to quickly permeate through, and a highly water-absorbing polymer disposed between two sheets interposed between the sheets 2 and 3, and side non-woven fabrics 7, 7 respectively arranged along the longitudinal direction on both side portions of the surface. Furthermore, in the periphery of the absorber 4, in the front and back edge portions in the longitudinal direction of the napkin, the outer edge portions of the liquid-impermeable back-surface sheet 2 and the liquid-permeable front-surface sheet 3 are joined to each other with an adhesive such as a hot melt or an adhesive means such as a heat seal, and in the both side edge portions, the liquid-impermeable back-surface sheet 2 and the side non-woven fabrics 7 extending out laterally as compared with the absorber 4 are joined with each other with an adhesive such as a hot melt or an adhesive means such as a heat seal, and an outer peripheral flap portion which is not provided with the absorber 4 on the outer periphery.

The structure of the sanitary napkin 1 will be described in more detail below.

As the liquid-impermeable back-surface sheet 2, a sheet material, for example, olefin resins such as polyethylene or polypropylene, having at least water-shielding property is used; alternatively, a laminate non-woven fabric sheet in which a non-woven fabric is stacked on polyethylene sheet and the like, a non-woven fabric in which a waterproof film is interposed to substantially secure liquid imperviousness (in this case, the waterproof film and the non-woven fabric constitute the liquid-impermeable back-surface sheet), or the like, can be used. In recent years, from the viewpoint of preventing stuffiness, a sheet having moisture permeability has tended to be used. The water-shielding and moisture-permeable sheet material is a microporous sheet obtained by melting and kneading an inorganic filler into an olefin resin such as polyethylene or polypropylene to mold a sheet, followed by stretching the resulting sheet in a uniaxial or biaxial direction.

Then, as the liquid-permeable front-surface sheet 3, a porous or non-porous non-woven fabric, a porous plastic sheet, or the like, is preferably used. As the material fiber of the non-woven fabric, for example, a synthetic fiber such as olefin such as polyethylene or polypropylene, polyester or polyamide, a regenerated fiber such as rayon and cupra or a natural fiber such as cotton can be used; a non-woven fabric obtained by an appropriate processing method such as a spun lace method, a spun bond method, a thermal bond method, a melt-blown method or a needle punching method can be used. Among these processing methods, the spun lace method is excellent in flexibility, a spun bond method is excellent in high draping property, the thermal bond method and the air-through method is excellent in bulkiness and compression resilience. The liquid-permeable front-surface sheet 3 may not be provided when an upper layer sheet 10 of the absorber 4 mentioned below constitutes a skin-contact surface layer.

The absorber 4 interposed between the liquid-impermeable back-surface sheet 2 and the liquid-permeable front-surface sheet 3 has a structure in which highly a water-absorbing polymer 12 is disposed between the upper layer sheet 10 disposed at a skin side and the lower layer sheet 11 disposed at a non-skin side 11.

As the upper layer sheet 10, a porous or non-porous non-woven fabric, a porous plastic sheet or the like is used. As the material fiber of the non-woven fabric, similar to the liquid-permeable front-surface sheet 3, for example, a synthetic fiber such as olefin such as polyethylene or polypropylene, polyester or polyamide, a regenerated fiber such as rayon and cupra or a natural fiber such as cotton can be used. The processing method of the non-woven fabric is not particularly limited, but in order to prevent a highly water-absorbing polymer 12 from dropping off, processing methods such as a spun bond method, a melt-blown method, a needle punching method, and the like, in which the fiber density of the resulting product is increased, are preferable. An opening diameter of the porous plastic sheet is preferably made smaller than the outer shape of the highly water-absorbing polymer 12 in order to prevent the highly water-absorbing polymer 12 from dropping off. Furthermore, as mentioned later in detail, since the upper layer sheet 10 is subjected to predetermined processing for making recesses and projections, it preferably includes thermoplastic materials.

As the lower layer sheet 11, a water-shielding seal material can be used in addition to the porous or non-porous non-woven fabric, a porous plastic sheet or the like. Similar to the upper layer sheet 10, the processing method of the non-woven fabric is not particularly limited, but in order to prevent a highly water-absorbing polymer 12 from dropping off, processing methods such as a spun bond method, a melt-blown method, a needle punching method, and the like, in which the fiber density of the resulting product is increased, are preferable. An opening diameter of the porous plastic sheet is preferably smaller than the outer shape of the highly water-absorbing polymer 12 in order to prevent the highly water-absorbing polymer 12 from dropping off. As the water-shielding seal material, material same as that of the liquid-impermeable back-surface sheet 2 can be used.

Examples of the highly water-absorbing polymer 12 include a polyacrylate cross-linked product, a self-cross-linked polyacrylic acid salt, a saponified product of acrylic acid ester-vinyl acetate copolymer cross-linked product, an isobutylene-maleic anhydride copolymer cross-linked product, a polysulfone salt cross-linked product, and a product obtained by partially cross-linking a water-swellable polymer such as polyethylene oxide or polyacrylamide. Among them, an acrylic acid and an acrylic acid salt excellent in the absorbed amount of water and the absorption speed of water are preferable. In the highly water-absorbing polymer having the absorption performance described above, in its manufacturing process, a cross-linking density and a cross-linking density gradient are adjusted, and thus it is possible to adjust water absorption power and a water absorption speed.

On the other hand, in both side portions on the surface side of the sanitary napkin 1, the side non-woven fabrics 7, 7 are provided along the longitudinal direction and over the substantially entire length of the napkin 1, and a part of the side non-woven fabrics 7, 7 is extended laterally, and forms wing-shaped flaps W, W together with a part of the liquid-impermeable back-surface sheet 2 that is similarly extended laterally.

As the side non-woven fabric 7, from the viewpoint of function on which importance is placed, it is possible to use a water-repellent or hydrophilic non-woven fabrics. For example, when importance is placed on functions such as preventing the penetration of menstrual blood and vaginal discharge or increasing favorable skin touch, it is desirable to use water-repellent non-woven fabrics coated with silicon-based, paraffin-based, or alkyl chromic chloride-based water repellent, or the like. Furthermore, when importance is placed on the absorption of menstrual blood and the like by the wing-shaped flaps W, W, it is desirable to use hydrophilic non-woven fabrics obtained by allowing synthetic fibers to be swollen or to be porous by a method of allowing a compound, such as oxidation products of polyethylene glycol or the like, having a hydrophilic group to coexist and be polymerized in the manufacturing process of synthetic fiber, or a method of treating the compound with a metal salt such as stannic chloride to make the surface thereof partially dissolve to be porous and to deposit metal hydroxides, or the like, and providing hydrophilic property by means of a capillary phenomenon.

At the inner side of the side non-woven fabrics 7, as shown in FIG. 2, stereoscopic gathers BS, BS are formed by folding back the side non-woven fabrics 7 substantially in two, disposing one or a plurality of (two in the drawing) filamentous resilient and elastic members 8, 8 with the both ends or appropriate positions in the longitudinal direction fixed to the intermediate portion in the height direction, to the inside of this double sheets, and allowing the sheet portion to stand toward the skin side by the contracting force.

Absorber 4

Hereinafter, the absorber 4 will be described in detail. As shown in FIGS. 3 to 5, the absorber 4 has a structure including an upper layer sheet 10 disposed at a skin side (a liquid-permeable front-surface sheet 3 side), a lower layer sheet 11 disposed at a non-skin side (a liquid-impermeable back-surface sheet 2 side), and a highly water-absorbing polymer 12 interposed therebetween.

The upper layer sheet 10 is provided with a plurality of protruding portions 14 bulging out to the skin side and forming space portion 13 to be filled with the highly water-absorbing polymer 12. In other words, the upper layer sheet 10 is formed in recesses and projections including a large number of the protruding portions 14, 14 . . . bulging out to the skin side. On the other hand, the lower layer sheet 11 is formed in a flat planar shape. Consequently, in a state in which the lower layer sheet 11 is stacked on the non-skin side of the upper layer sheet 10, the space portions 13 are formed inside the protruding portions 14 between the upper layer sheet 10 and the lower layer sheet 11. Thus, a predetermined amount of highly water-absorbing polymer 12 is contained in space portions 13.

The upper layer sheet 10 and the lower layer sheet 11 are joined to each other by the joined portions 15, 15 . . . which are intermittently disposed along a circumferential direction in a portion in which the upper layer sheet 10 on the peripheral edge of the protruding portion 14 is projected toward the non-skin side. The intermittent parts of the joined portions 15, 15, which are adjacent to each other along the circumferential direction of the protruding portion 14, form a non-joined portion 16 in which the upper layer sheet 10 and the lower layer sheet 11 are not joined to each other. In other words, the peripheral edge of the protruding portion 14 is an intermittent joined portion in which the joined portion 15, in which the upper layer sheet 10 and the lower layer sheet 11 are joined to each other, and the non-joined portion 16, in which the upper layer sheet 10 and the lower layer sheet 11 are not joined to each other, are disposed alternately along the circumferential direction.

The joined portion 15 may be obtained by joining upper layer sheet 10 and the lower layer sheet 11 to each other by applying a hot-melt adhesive, and by fusing the upper layer sheet 10 and the lower layer sheet 11 by heating or ultrasonic radiation at the time of compression from the outside of upper layer sheet 10.

The adjacent space portions 13, 13 are partitioned by the joined portions 15 (FIG. 4), and communicate with each other through the non-joined portions 16 (FIG. 5). Therefore, in the joined portions 15, a body fluid is blocked, thus making it difficult for a body fluid to move into the adjacent space portions 13. However, in the non-joined portion 16, a body fluid can easily move to the adjacent space portions 13 through a gap between the upper layer sheet 10 and the lower layer sheet 11.

The diffusion state of the body fluid will be described based on FIG. 6. FIG. 6A shows a case where peripheral edges of the protruding portions are continuously joined, which is not included in the present invention. FIG. 6B shows a case where the peripheral edges of the protruding portions 14 are intermittently joined according to the present invention. As shown in FIG. 6A, the peripheral parts are joined by continuous joined portions, a body fluid are blocked by the joined portion, and does not diffuse to the adjacent space portions. Consequently, the body fluid is absorbed by a highly water-absorbing polymer of a part of the space portion, thus deteriorating absorption efficiency. The amount of polymer absorbed by this part of the space portion is extremely increased, and at the time of water absorption, this part bulge to the skin side more remarkably larger than surrounding area, thus easily causing uncomfortable feeling at the time of wearing. In addition, pressure is concentrated on this bulging part, thus easily causing occurrence of return.

On the contrary, as shown in FIG. 6B, in the sanitary napkin 1 according to the present invention, since the surrounding of the space portion 13 is joined through an intermittent joined portion in which the joined portion 15 and non-joined portion 16 are alternately arranged, a body fluid does not easily diffuse in the joined portion 15 but easily diffuses to the adjacent space portion 13 through the non-joined portion 16. Therefore, the body fluid is absorbed into the wide range of the highly water-absorbing polymer 12, resulting in improving the absorption efficiency, and enabling the body fluid to be absorbed quickly. Furthermore, since the body fluid is dispersed in a wide range and absorbed, at the time of absorption of the highly water-absorbing polymer 12, it is possible to prevent the occurrence of uncomfortable feeling at the time of wearing or return by concentration of pressure. Furthermore, the peripheral part of the space portion 13 is partitioned by joined portions 15, 15 . . . intermittently disposed along the circumferential direction 14 at the peripheral edges of the protruding portion 14, a state in which the highly water-absorbing polymer 12 is contained inside can be retained, thus enabling a stable absorption amount to be maintained.

In the intermittent joined portions provided at the peripheral edge of the protruding portion 14, it is preferable that a separated distance along the circumferential direction of the adjacent joined portions 15, 15 (a length along the circumferential direction of the non-joined portion 16) is smaller than three times as large as the average particle diameter of the highly water-absorbing polymer 12 before water is absorbed. Thus, it is possible to prevent the highly water-absorbing polymer 12 before water is absorbed, from moving on the flow of a body fluid into the adjacent space portions 13 through the non-joined portion 16, the filling rate of polymer in each space portion 13 can be kept constant. It is preferable that the length of the non-joined portion 16 is smaller than the average particle diameter of the highly water-absorbing polymer 12 from the viewpoint of preventing the outflow of the highly water-absorbing polymer 12 from the non-joined portion 16. However, since the average particle diameter of the highly water-absorbing polymer 12 is about 300 to 500 μm, the length of the non-joined portion 16 may be larger than the average particle diameter of the highly water-absorbing polymer 12 for the following reasons. (1) When the length of the non-joined portion 16 is made smaller than the average particle diameter of polymers, restriction in design of an emboss roller for forming the non-joined portion 16 is increased. (2) Since the upper layer sheet 10 and the lower layer sheet 11 are joined to each other with the joined portions 15, 15 adjacent to both ends of the non-joined portion 16, a gap between the upper layer sheet 10 and the lower layer sheet 11 of the non-joined portion 16 is kept small, even before water is absorbed, flowing of the highly water-absorbing polymer 12 does not easily occur. (3) Furthermore, the highly water-absorbing polymer 12 starts to swell at the time when it is brought into contact with a body fluid, although the absorption speed is slow. Therefore, even when the length of the non-joined portion 16 is larger than the average particle diameter of the polymer, the polymer does not easily flow on the flow of the body fluid.

Note here that the average particle diameter of the highly water-absorbing polymer particles before water is absorbed means a particle diameter at 50% of the integrated value in the weight particle size distribution. The weight particle size distribution in this case is measured according to JIS Z8815-1994. Sieves having inner diameter of 150 mm and a depth of 45 mm with opening sizes of 710 μm, 500 μm, 300 μm, 150 μm, and 106 μm are plied one on another with a sieve having smaller opening size placed at a lower position. Then, 50 g of a measurement sample is put on the top sieve having the largest in opening size, i.e., 710 μm, and is shaken for 10 minutes by a sieve shaker. Subsequently, the measurement sample remaining on each sieve is weighed and the percentage by weight of the measurement sample remaining on each sieve based on the weight of the initial measurement sample is calculated, so that the particle size distribution was determined.

It is preferable that the intermittent joined portion provided on the peripheral edge of the protruding portion 14 is provided along the planar shape of the protruding portion 14. The joined portion 15 can be formed in an appropriate shape such as linear, curvilinear or dotted shape. In FIG. 3, linear joined portions 15 are formed at equally spaced intervals in the longitudinal direction and the width direction of the absorber 4, respectively so as to surround the peripheral edge of square protruding portions 14 arranged in lattice.

In a case where the square protruding portions 14 are arranged in lattice, as shown in FIG. 3, protruding portions 14 may be arranged such that the joined portions 15 along the longitudinal direction and the width direction intersect to each other at the intersections in lattice. Alternatively, as shown in FIG. 7, protruding portions 14 may be arranged such that non-joined portions 16 intersect to each other at the intersections in lattice. Furthermore, both of them may be combined in arrangement.

It is preferable that the intermittent joined portion is provided with one or more non-joined portions 16 with respect to at least in the longitudinal direction of the absorber 4 among the peripheral edge of the protruding portion 14. This makes it possible to allow a body fluid in the space portions 13 to diffuse at least in the longitudinal direction of the absorber 4 through the non-joined portions 16. Furthermore, as shown in FIGS. 3 and 7, the non-joined portions 16 are preferably provided in both the longitudinal direction and the width direction of the absorber 4 in the peripheral edge of the protruding portion 14. This makes it possible to increase the degree of freedom in the direction of diffusion of the body fluid. However, when a body fluid diffusion restriction joined portion, which is described later in detail, is provided, it is preferable that the non-joined portion 16 is not provided in the direction thereof.

It is preferable that the protruding portions 14 are provided in such a pattern that a plurality of the protruding portions 14 are arranged in a plane of the absorber 4 in the longitudinal direction and the width direction, respectively. Thus, since the absorber 4 is partitioned by a plurality of space portions 13, 13 . . . in the longitudinal direction and the width direction, respectively, it is possible to prevent the highly water-absorbing polymer 12 contained in each space portion 13 from being distributed largely unevenly. In the process in which the body fluid sequentially diffuses to adjacent space portions 13, the body fluid is absorbed by the highly water-absorbing polymer 12 contained in each space portion 13. Thus, a stable amount of absorbed fluid can be secured.

The average dimension of the protruding portion 14 is preferably 5 mm to 20 mm with respect to the longitudinal direction of the absorber 4, and 3 mm to 15 mm in the width direction of the absorber 4.

In an example shown in FIG. 3, the protruding portions 14 are disposed in substantially equal size over the width direction and the longitudinal direction of the absorber 4, respectively. However, as shown in FIG. 8, the sizes of the protruding portions 14 may be changed depending on the sites of the absorbers 4. For example, as shown in FIG. 8, in a region corresponding to a blood discharge port of a wearer, the protruding portions 14 can be formed in relatively small planar shapes so that the highly water-absorbing polymer 12 is prevented, as much as possible, from being distributed largely unevenly inside the space portion 13, the body fluid and the highly water-absorbing polymer 12 are brought into contact with each other efficiently, and the body fluid can be absorbed by the highly water-absorbing polymer 12 quickly. In FIG. 8A, the protruding portions 14 having a relatively small planar shape are provided around a blood discharge port of a wearer as a center over the longitudinal direction and the width direction of the absorber 4, respectively, and in the intersection regions thereof corresponding to the blood discharge port, a planar shape of the protruding portion 14 is made to be further smaller. In FIG. 8B, protruding portions 14 having a relatively small planar shape are provided only in a region corresponding to the blood discharge port of a wearer.

The planar shape of the protruding portion 14 can be one or a combination of two or more selected from the group consisting of a polygon such as square, hexagon, and octagon, a rhombus, a circle, an ellipse, and an hourglass shape. In other words, a planar shape of the protruding portion 14 is not necessarily configured by one shape, and may be configured by a combination of two or more shapes. For example, in FIG. 9A, circular or elliptical-shaped first protruding portions 14a, 14a . . . are disposed in lattice such that they are arranged in the width direction and the longitudinal direction of the absorber 4, respectively, and rhombus second protruding portion 14b is disposed in a region with four corners surrounded by the first protruding portions 14a, 14a . . . . Furthermore, in FIG. 9B, circular or elliptical-shaped first protruding portions 14c, 14c . . . are continuously disposed in the longitudinal direction of the absorber 4 and at predetermined spaced intervals in the width direction, and substantially hourglass-shaped second protruding portions 14d, 14d . . . are continuously formed in a portion whose both sides are surrounded by the first protruding portions 14c, 14c in the longitudinal direction. In this way, when protruding portions 14 having different planar shapes are provided, a body fluid diffuses in the adjacent protruding portions 14 having different planar shapes, so that the body fluid can be easily absorbed by the highly water-absorbing polymer 12 inside.

The cross-sectional shape of the protruding portion 14 may be a rectangular cross section having a substantially flat surface as shown in FIGS. 4 and 5, a curvilinear cross section bulging in a dome shape toward the skin side, or a cone-shaped cross section having a linear slope surface toward the skin side. Furthermore, the protruding portion 14 is formed by two types or more of planar shapes, cross-sectional shapes of the protruding portions may be the same as or different form each other.

The joined portions 15 can be formed in a substantially equal length along the entire periphery of the protruding portion 14, or can be formed by combining the joined portions 15 having different lengths. Combining the joined portions 15 having different lengths enables the joining strength between the upper layer sheet 10 and the lower layer sheet 11 to be adjusted, diffusion of the direction of the body fluid to be controlled, or the diffusion rate to be adjusted.

As shown in FIG. 10, as the joined portion 15, in order to control a diffusion direction of a body fluid, it is possible to provide a liquid-diffusion restriction joined portion 17 that is relatively longer than the other joined portions. As shown in FIG. 10, the liquid-diffusion restriction joined portion 17 preferably includes liquid-diffusion restriction joined portions 17a provided along the longitudinal direction respectively on both side portions in the width direction of at least a region corresponding to a blood discharge port of a wearer. Thus, diffusion of the body fluid discharged from the blood discharge port toward the width direction is restricted by the liquid-diffusion restriction joined portions 17a, 17a provided on both sides, and the body fluid easily diffuses in the longitudinal direction. Consequently, leakage of the body fluid from the both sides in the width direction can be prevented. Furthermore, as shown in FIG. 10, it is preferable that the liquid-diffusion restriction joined portion 17 includes liquid-diffusion restriction joined portions 17b which extend in the width direction over separated portions in the width direction of the liquid-diffusion restriction joined portions 17a, 17a provided at both sides of the blood discharge port, and which are provided respectively along the width direction such that they are separated outward from the liquid-diffusion restriction joined portions 17a, 17a in the front-and-back direction; and also includes liquid-diffusion restriction joined portions 17c, 17c . . . which extend in the front-and-back direction over separated portions in the front-and-back direction of the liquid-diffusion restriction joined portions 17a provided at both sides of the blood discharge port, and the liquid-diffusion restriction joined portions 17b separately provided in the front and back sides of the liquid-diffusion restriction joined portions 17a, and which are provided respectively along the front-and-back direction such that they are separated outward in the width direction from the liquid-diffusion restriction joined portions 17a and 17b. By providing the liquid-diffusion restriction joined portions 17a and 17b, the body fluid that is promoted to diffuse in the front-and-back direction by the liquid-diffusion restriction joined portion 17a is changed to diffusion in the with direction by the liquid-diffusion restriction joined portion 17b, and diffusion is changed again to the diffusion to the front-and-back direction by the liquid-diffusion restriction joined portion 17c, so that the body fluid can be allowed to diffuse in a zig-zag manner, the body fluid can be allowed to diffuse in a wider range, and the body fluid can be absorbed by the highly water-absorbing polymer 12 efficiently quickly.

Furthermore, as shown in FIG. 11, in a pattern in which the above-mentioned elliptical-shaped first protruding portions 14a are arranged in a lattice, and rhombus second protruding portions 14b are provided respectively in regions four corners of which are surrounded by the first protruding portions 14a, 14a . . . , respectively, the liquid-diffusion restriction joined portions 17 being relatively longer are provided to the first protruding portions 14a at both sides in the width direction of the absorber 4 and both end portions in the longitudinal direction. Dotted joined portions 15, 15 . . . can be provided in the oblique direction portion other than the above. Thus, diffusion of a body fluid moving straight in the width direction and the longitudinal direction of the absorber 4 provided with the liquid-diffusion restriction joined portion 17 is restricted, and the body fluid can easily diffuse in the oblique direction through a non-joined portion 16 between the portion 17 and the dotted joined portions 15, in other words, in a direction in which the second protruding portion 14b is disposed. Thus, in a process in which the body fluid diffuses, the body fluid is absorbed by the highly water-absorbing polymer 12 contained in each space portion 13 of the first protruding portions 14a and the second protruding portion 14b. Therefore, the body fluid can be absorbed efficiently quickly.

The length of the liquid-diffusion restriction joined portion 17 is preferably twice to ten times as long as the length of the other joined portions 15. Furthermore, the width of the liquid-diffusion restriction joined portion 17 may be equal to the width of the joined portion 15, and may be wider for enhancing the effect of limiting liquid diffusion.

On the other hand, as shown in FIG. 12, a liquid guiding joined portion 18 can be provided by disposing the joined portions 15, 15 of the adjacent protruding portions 14, 14 in parallel at a predetermined spaced interval. The liquid guiding joined portion 18 allows the body fluid to diffuse along a portion between the joined portions 15, 15 disposed in parallel, thereby controlling the diffusion direction of the body fluid. The liquid guiding joined portion 18 is configured to enhance the diffusion property of the body fluid. Disposing of the joined portions 15, 15 in parallel in the liquid guiding joined portion 18 is a concept including not only arranging linearly-formed joined portions 15, 15 in parallel but also arranging the joined portions 15, 15 such that directions along which curvilinearly-formed joined portions 15, 15 are provided become in parallel, as shown in FIG. 12. Furthermore, in FIG. 12, the joined portions 15, 15 are formed such that the projected portion sides face in a back-to-back manner, but the joined portions 15, 15 may be formed such that the recess portion sides face in a front-to-front manner, or may be disposed in parallel such that joined portions 15, 15 projected toward the same direction. Specifically, in FIG. 12, elliptical-shaped first protruding portions 14e, which are provided with arc-shaped joined portions 15 in the width direction and the longitudinal direction respectively, along the circumferential direction, are arranged in lattice at a predetermined spaced interval in the width direction and the longitudinal direction, and rhombus second protruding portions 14*f* are provided in a region whose four corners are surrounded by the first protruding portions 14*e*, 14*e* . . . , to form a pattern. The arc-shaped joined portions 15, 15 of the adjacent the first protruding portions 14*e*, 14*e* form the liquid guiding joined portion 18. Thus, as shown in FIG. 12, the body fluid flowing into the second protruding portion 14*f* diffuses into the adjacent first protruding portions 14*e* through the non-joined portion 16 in the oblique direction, and also diffuses to the adjacent second protruding portions 14*f* along the portion between the joined portions 15, 15 constituting the liquid guiding joined portion 18, the diffusion property of the body fluid can be enhanced also in the width direction and the longitudinal direction.

In order to prevent the highly water-absorbing polymer 12 contained inside from dropping off, the protruding portion 14 is preferably provided in an intermediate region that does not reach the end portions in the longitudinal direction and the width direction of the upper layer sheet 10 and the lower layer sheet 11.

As shown in FIG. 3, in the peripheral edge portion of the absorber 4, in order to prevent the highly water-absorbing polymer 12 contained in the space portion 13 from dropping off, it is preferable to provide a peripheral edge joined portion 19 in which the upper layer sheet 10 and the lower layer sheet 11 are continuously joined to each other along the circumferential direction of the absorber 4. As shown in FIG. 3, this peripheral edge joined portion 19 may constitute a part of the intermittent joined portion provided in the peripheral edge of protruding portion 14 disposed in the peripheral edge portion of absorber 4. Although not shown in the drawing, the peripheral edge joined portion 19 may be provided separately outside the intermittent joined portion provided at the peripheral edge of the protruding portion 14.

Note here that a polymer filling rate R (R=P/V×100%) as a ratio of a volume V of the space portion 13 to a volume P of the highly water-absorbing polymer 12 to be filled in the space portion 13 is preferably 10% or more and 70% or less. The polymer filling rate R of less than 10% makes the absorption efficiency of the body fluid poor, and the polymer filling rate R of more than 70% makes it difficult for the body fluid to move between polymers, and thus the diffusion property of the body fluid may be deteriorated in the space portion 13. When the space portion 13 is filled with the highly water-absorbing polymer 12 at a predetermined polymer filling rate R, a space when the highly water-absorbing polymer 12 is wetted and swelled can be secured, and cushion property can be provided by the space inside the space portion 13 before water is absorbed.

Weight of the highly water-absorbing polymer 12 to be filled in the space portion 13 is 20 to 300 $g/m^2$, and preferably 80 to 200 $g/m^2$.

For manufacturing the absorber 4, as shown in FIGS. 13 and 14, it is preferable to use a manufacturing device 20 of allowing the upper layer sheet 10 to pass between a first emboss roller 21 in which a large number of projected portions 21*a*, 21*a* . . . corresponding to the protruding portions 14 are arranged, and a second emboss roller 22 in which a large number of recess portions 22*a*, 22*a* . . . corresponding to the projected portions 21*a* are arranged, thereby forming the protruding portions 14 by engagement between the projected portion 21*a* and the recess portion 22*a*.

Thereafter, the highly water-absorbing polymer 12 is dispersed on the surface of the second emboss roller 22 having the upper layer sheet 10 thereon to allow the highly water-absorbing polymer 12 to be contained in a recess portion. The upper layer sheet 10 in a state in a state in which the lower layer sheet 11 fed from a different route is stacked is allowed to pass between the second emboss roller 22 and the flat roller 23. Thereby the upper layer sheet 10 and the lower layer sheet 11 are joined and integrated to each other by the joined portion 15 and the peripheral edge joined portion 19. For joining thereof, for example, a hot-melt adhesive is applied to the outer surface of the upper layer sheet 10 corresponding to the projected portion of the second emboss roller 22, and the upper layer sheet 10 is adhesively bonded to the lower layer sheet 11. Alternatively, the upper layer sheet 10 and the lower layer sheet 11 may be fused to each other by heating or ultrasonically radiating the projected portions of the second emboss roller 22 at the time of engagement with the flat roller 23.

Providing a suction port to the bottom portion of a recess portion 22*a* of the second emboss roller 22 facilitates suction and embossing of the upper layer sheet 10 at the time of embossing, and enables the highly water-absorbing polymer 12 to be sucked at the time of dispersion to prevent the polymer from dropping off. Furthermore, after dispersion of the highly water-absorbing polymer 12, the surface is averaged by a scraper to adjust the amount of highly water-absorbing polymer 12 that is contained in the space portion 13.

Thereafter, as shown in FIG. 15, absorbers 4, 4 . . . that are continuous in the longitudinal direction is cut at a joined portion, which is not provided with the protruding portion 14, between upper layer sheet 10 and the lower layer sheet 11.

As shown in FIG. 2, the absorber 4 may be interposed as a simple substance between the liquid-permeable front-surface sheet 3 and the liquid-impermeable back-surface sheet 2. Alternatively, as shown in FIGS. 16 and 17, the absorber 4 may be interposed as a stack with a fiber aggregate layer 30 including a water-absorbing fiber aggregate such as a pulp disposed at a non-skin side or a skin side of the absorber 4. The fiber aggregate layer 30 may be formed of at least a water-absorbing fiber aggregate, and may contain a highly water-absorbing polymer.

In FIG. 16, the fiber aggregate layer 30 is disposed on the non-skin side of the absorber 4, and a stacked body of the absorber 4 and the fiber aggregate layer 30 is interposed between the liquid-permeable front-surface sheet 3 and the liquid-impermeable back-surface sheet 2. Thus, a body fluid permeating through the absorber 4 as an upper layer is absorbed and retained by fiber aggregate layer 30 as a lower layer. In this case, as the lower layer sheet 11 constituting the absorber 4, a water permeable seal material is preferably used.

In FIG. 17, the fiber aggregate layer 30 is disposed at the skin side of the absorber 4, and a stacked body of the absorber 4 and the fiber aggregate layer 30 is interposed between the liquid-permeable front-surface sheet 3 and the liquid-impermeable back-surface sheet 2. Thus, the body fluid that diffuses in the fiber aggregate layer 30 can be absorbed by the absorber 4 quickly. In this case, as shown in FIG. 17, a slit 31 penetrating in the longitudinal direction may be provided along a middle part in the width direction of the fiber aggregate layer 30. Thus, this slit 31 works as a transient storage space of a body fluid, and the body fluid is allowed to diffuse in the longitudinal direction along the slit 31, and in the absorber 4, the body fluid can diffuse.

Therefore, excellent diffusion property is achieved and a body fluid can be absorbed by the absorber 4 efficiently quickly.

When the absorber 4 and the fiber aggregate layer 30 are stacked onto each other to form a stacked body, the absorber 4 is not necessarily disposed on the entire surface of the fiber aggregate layer 30. For example, the absorber 4 can be disposed only in a middle region of a napkin having a blood discharge port, or only in a cyclic region surrounding the blood discharge port. In this case, the fiber aggregate layer 30 is disposed to the outer peripheral part of the sanitary napkin 1 with the outer peripheral flap part left.

Furthermore, although not shown in the drawings, the liquid-permeable front-surface sheet 3 is not necessarily an essential element, when the upper layer sheet 10 of the absorber 4 functions as a skin-contact surface layer, the liquid-permeable front-surface sheet 3 may not be disposed. Thus, the sanitary napkin 1 can further be thinned, and the number of material members can be reduced, thus enabling the cost to be reduced.

Other Exemplary Embodiment

In the above-mentioned exemplary embodiment, an example in which two types of protruding portions, i.e., first protruding portions and second protruding portions are provided, is shown (FIG. 9), but three types or more protruding portions may be provided.

REFERENCE MARKS IN THE DRAWINGS

1 . . . sanitary napkin
2 . . . liquid-impermeable back-surface sheet
3 . . . liquid-permeable front-surface sheet
4 . . . absorber
7 . . . side non-woven fabric
10 . . . upper layer sheet
11 . . . lower layer sheet
12 . . . highly water-absorbing polymer
13 . . . space portion
14 . . . protruding portion
15 . . . joined portion
16 . . . non-joined portion
17 . . . liquid-diffusion restriction joined portion
18 . . . liquid guiding joined portion
19 . . . peripheral edge joined portion

The invention claimed is:

1. An absorbent article comprising an absorber, which comprises an upper layer sheet disposed at a skin side, a lower layer sheet disposed at a non-skin side, and a highly water-absorbing polymer disposed between the upper layer sheet and the lower layer sheet,
   wherein the upper layer sheet comprises:
   a plurality of protruding portions bulging out to the skin side and forming space portions to be filled with the highly water-absorbing polymer,
      wherein the plurality of the protruding portions is arranged in a plane of the absorber in the longitudinal direction and the width direction, respectively,
      a planar shape of the protruding portions is a square shape, and
      a region of the absorbent article corresponding to a blood discharge port comprises protruding portions having a square area smaller than in a region not corresponding to the blood discharge port,
   joined portions in which the upper layer sheet and the lower layer sheet are joined to each other intermittently on peripheral edges of the protruding portions along a circumferential direction,
   first liquid-diffusion restriction joined portions provided along a longitudinal direction on both side portions in a width direction of at least a region corresponding to a blood discharge port of a wearer,
   second liquid-diffusion restriction joined portions which extend in the width direction over separated portions in the width direction of the first liquid-diffusion restriction joined portions provided at both sides of the blood discharge port, and which are provided respectively along the width direction such that they are separated outward from the first liquid-diffusion restriction joined portions in the front-and-back direction, and
   third liquid-diffusion restriction joined portions which extend in the front-and-back direction over separated portions in the front-and-back direction of the first liquid-diffusion restriction joined portions provided at both sides of the blood discharge port, and the second liquid-diffusion restriction joined portions separately provided in the front and back sides of the first liquid-diffusion restriction joined portions, and which are provided respectively along the front-and-back direction such that they are separated outward in the width direction from the first and second liquid-diffusion restriction joined portions,
   wherein a length of the first, second and third liquid-diffusion restriction joined portions is two to ten times as long as a length of the joined portions, and
   wherein a separated distance along a circumferential direction of adjacent joined portions is larger than an average particle diameter of the highly water-absorbing polymer before water is absorbed and smaller than three times the average particle diameter.

2. The absorbent article according to claim 1, further comprising a liquid guiding joined portion in which the joined portions, being respectively disposed at peripheral edges of the protruding portions adjacent to each other, are arranged in parallel at a predetermined spaced interval.

3. The absorbent article according to claim 1, further comprising a peripheral edge joined portion in which the upper layer sheet and the lower layer sheet are joined to each other continuously on the peripheral edge portion of the absorber along a circumferential direction.

4. The absorbent article according to claim 1, wherein a polymer filling rate that is a ratio of a volume of the space portion to a volume of the highly water-absorbing polymer to be filled in the space portion is 10% or more and 70% or less.

5. The absorbent article according to claim 1, further comprising a fiber aggregate layer comprising a water-absorbing fiber aggregate disposed at the non-skin side or the skin side of the absorber.

* * * * *